(12) United States Patent
Zhang (10) Patent No.: US 8,857,253 B2
(45) Date of Patent: Oct. 14, 2014

(54) MEASURING DEVICE FOR MEASURING ADHESIVE STRENGTH OF TWO-SIDED ADHESIVE TAPES

(75) Inventor: Bing-Jun Zhang, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 188 days.

(21) Appl. No.: 13/421,859

(22) Filed: Mar. 15, 2012

(65) Prior Publication Data

US 2013/0205885 A1 Aug. 15, 2013

(30) Foreign Application Priority Data

Feb. 14, 2012 (CN) .......................... 201210032215.2

(51) Int. Cl.
*G01N 19/04* (2006.01)
(52) U.S. Cl.
USPC ......... 73/150 A; 73/150 R; 156/378; 156/750
(58) Field of Classification Search
USPC ........... 73/150, 815, 826, 827, 829, 831, 835, 73/838, 841, 156, 842, 866, 796, 64, 378, 73/862.39, 150 A, 862.321, 862.08; 156/64, 378, 349; 29/828, 745; 33/628
See application file for complete search history.

(56) References Cited

U.S. PATENT DOCUMENTS

| 4,020,742 A | * | 5/1977 | Raymond | 409/218 |
| 2012/0191093 A1 | * | 7/2012 | Wong et al. | 606/79 |
| 2012/0192414 A1 | * | 8/2012 | Montena et al. | 29/828 |

* cited by examiner

*Primary Examiner* — Peter Macchiarolo
*Assistant Examiner* — Anthony W Megna Fuentes
(74) *Attorney, Agent, or Firm* — Novak Druce Connolly Bove + Quigg LLP (57) ABSTRACT

A measuring device for measuring adhesive strength of two-sided adhesive pieces includes a frame, a supporting apparatus fixed to the frame, and a positioning apparatus installed on the supporting apparatus. The frame includes a pull member slidably installed on the frame along a first direction. The supporting apparatus includes a base secured on the frame, and a supporting assembly slidably installed on the base along a second direction perpendicular to the first direction. The positioning apparatus includes a supporting plate slidably installed on the supporting assembly along a third direction perpendicular to the first and second directions, and a number of pulling blocks. Each adhesive piece is adhered between the supporting plate and a corresponding pulling block. Each pulling block is connected to the pull member to be pulled up to disengage from the supporting plate, thereby measuring the adhesive strength of the adhesive piece.

9 Claims, 10 Drawing Sheets

MEASURING DEVICE FOR MEASURING ADHESIVE STRENGTH OF TWO-SIDED ADHESIVE TAPES

CROSS-REFERENCE OF RELATED APPLICATION

Relevant subject matter is disclosed in a U.S. patent application, titled "POSITIONING DEVICE AND POSITIONING METHOD FOR TWO-SIDED ADHESIVE TAPES", with the application Ser. No. 13/418,371, filed on Mar. 13, 2012, which is assigned to the same assignee as this patent application.

BACKGROUND

1. Technical Field

The present disclosure relates to a device for measuring adhesive strength of two-sided adhesive tapes.

2. Description of Related Art

Currently, a method of measuring adhesive strength of a two-sided adhesive tape includes the following steps: cutting the adhesive tape into a number of pieces, adhering a first surface of each adhesive piece on a pulling block, manually adhering a second surface of the adhesive piece on a positioning block, pressing the pulling block with a predetermined pressure for a predetermined time, and measuring the adhesive strength of the two-sided adhesive tape through a two-sided adhesive viscosity tester. However, using the two-sided adhesive viscosity tester is time-consuming, and cannot satisfy mass-production demands.

BRIEF DESCRIPTION OF THE DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, all the views are schematic, and like reference numerals designate corresponding parts throughout the several views.

DETAILED DESCRIPTION

The present disclosure, including the accompanying drawings, is illustrated by way of examples and not by way of limitation. It should be noted that references to "an" or "one" embodiment in this disclosure are not necessarily to the same embodiment, and such references mean at least one.

Figure 1:
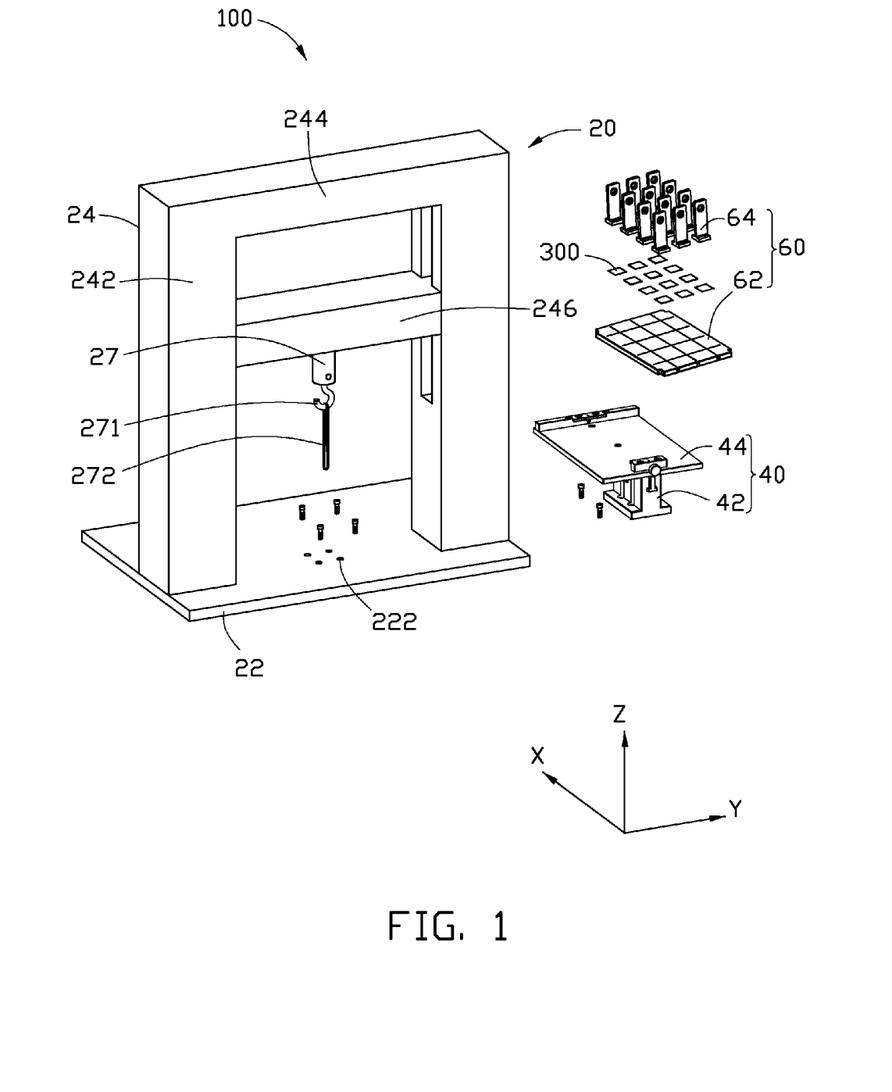
FIG. 1 is an exploded, isometric view of an exemplary embodiment of a measuring device and a plurality of two-sided adhesive pieces, the measuring device includes a base, a supporting assembly, and a positioning apparatus.

Referring to FIG. 1, an exemplary embodiment of a measuring device 100 for measuring adhesive strength of a plurality of two-sided adhesive pieces 300 cut from a two-sided adhesive tape includes a frame 20, a supporting apparatus 40, and a positioning apparatus 60.

The frame 20 includes a bottom wall 22, a substantially U-shaped rack 24 secured on the bottom wall 22 with opposite ends, and a pull member 27. The rack 24 includes two posts 242 substantially perpendicularly connected to the bottom wall 22 with bottom ends, and a connection bar 244 substantially perpendicularly connected between top ends of the posts 242. A beam 246 is substantially perpendicularly connected between the posts 242, below and substantially parallel to the connection bar 244. The beam 246 is slidable up and down relative to the posts 242 (which is labeled as Z-axis shown in FIG. 1). The pull member 27 is mounted to a bottom of the beam 244. The pull member includes a hook 271 facing the bottom wall 22, and a rope 272. The bottom wall 22 defines a plurality of screw holes 222, below the pull member 27.

The supporting apparatus 40 includes a base 42 and a supporting assembly 44.

Figure 2:
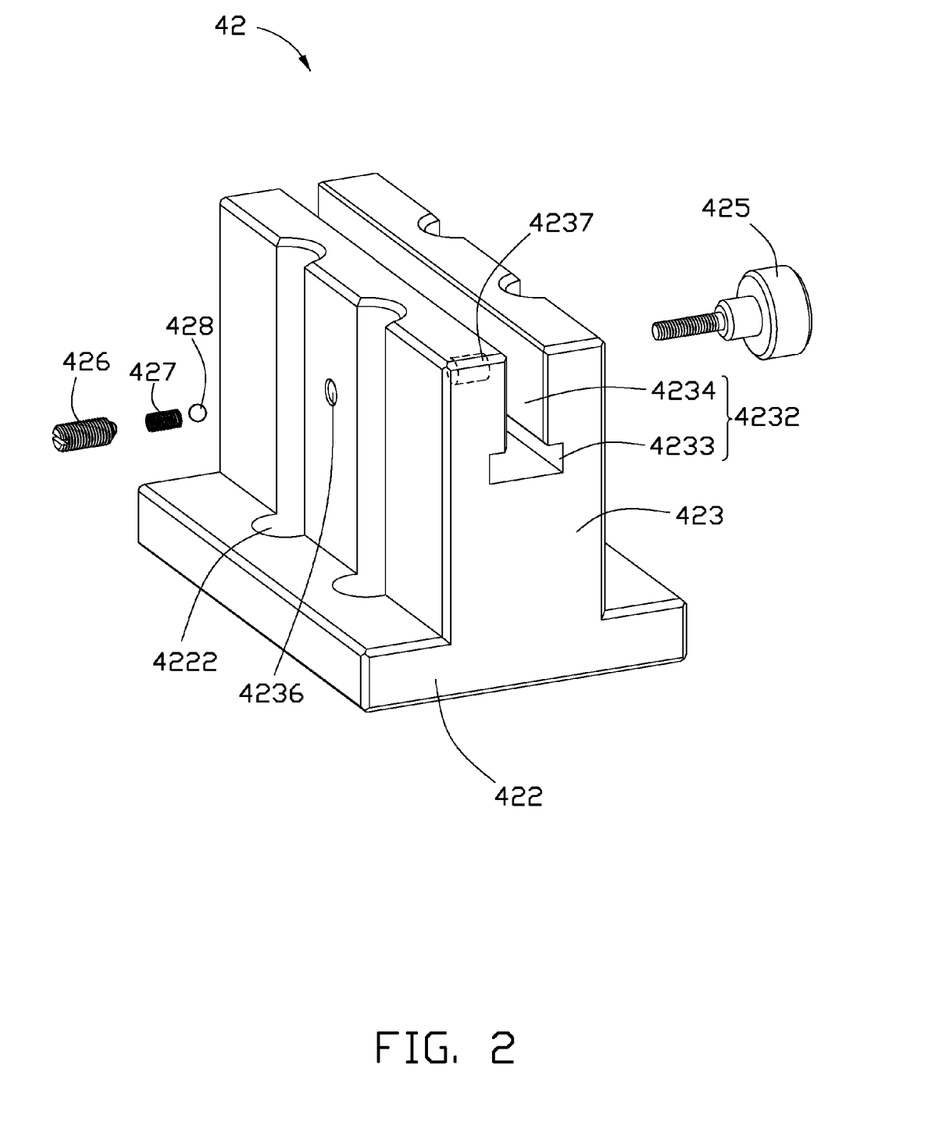
FIG. 2 is an exploded, isometric view of the base of FIG. 1.

Referring to FIG. 2, the base 42 is substantially T-shaped, and includes a rectangular connecting plate 422, an extending portion 423 substantially perpendicularly extending up from a middle of the connecting plate 422, a stopping screw 425, a positioning screw 426, an elastic member such as a spring 427, and a steel ball 428.

A junction of the connecting plate 422 and each of opposite side surfaces of the extending portion 423 define a plurality of through holes 4222. The through holes 4222 extend through the side surface and a top of the extending portion 423. A center of the top of the extending portion 423 defines a substantially T-shaped slide slot 4232 along a lengthwise direction of the extending portion 423. The slide slot 4232 includes a positioning portion 4233 extending through two opposite end surfaces of the extending portion 423, and a guiding portion 4234 communicating with the positioning portion 4233 and extending through the top and the end surfaces of the extending portion 423. A width of the positioning portion 4233 is greater than a width of the guiding portion 4234. One of the opposite side surfaces of the extending portion 423 defines a positioning hole 4236 communicating with the positioning portion 4233, and the other side surface defines a screw hole 4237 communicating with the positioning portion 4233. The positioning hole 4236 is tapered toward the slide slot 4232, and a diameter of an inner part of the positioning hole 4236 adjacent to the positioning portion 4233 is less than a diameter of the steel ball 428.

Figure 3:
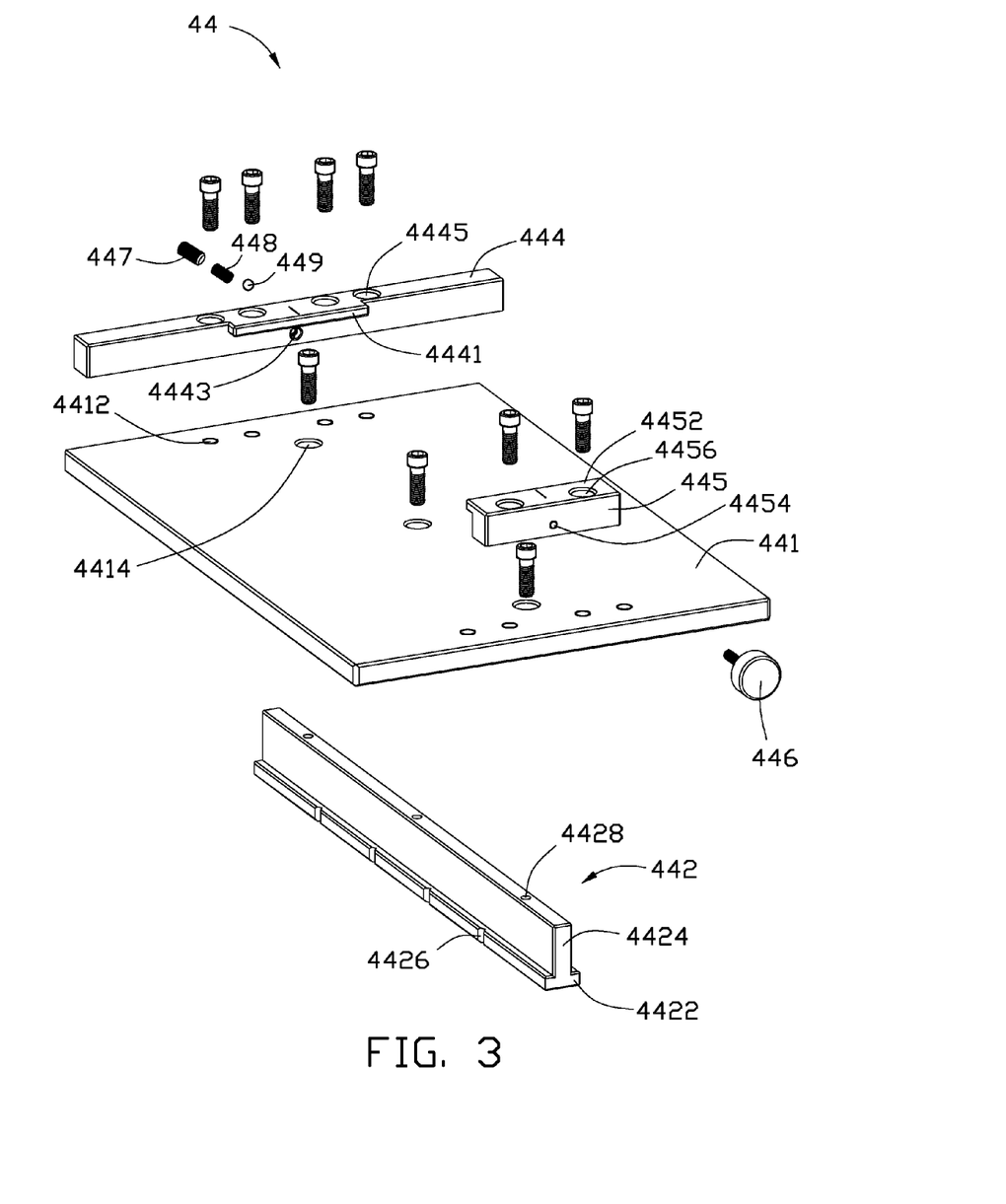
FIG. 3 is an exploded, isometric view of the supporting assembly of FIG. 1.

Referring to FIG. 3, the supporting assembly 44 includes a rectangular supporting portion 441, a substantially T-shaped rail 442, a first guiding bar 444, a second guiding bar 445, a stopping screw 446, a positioning screw 447, an elastic member such as a spring 448, and a steel ball 449. A top surface of the supporting portion 441 defines a plurality of screw holes 4412 in two opposite ends of the top surface, and defines a plurality of stopping holes 4414 in a middle of the top surface along a lengthwise direction of the supporting portion 441.

The rail 442 includes a rectangular positioning bar 4422 and a rectangular connecting bar 4424 perpendicularly extending up from a middle of the positioning bar 4422. Two opposite side surfaces of the positioning bar 4422 each define four positioning slots 4426 along a lengthwise direction of the positioning bar 4422. A top surface of the connecting bar 4424 defines a plurality of screw holes 4428.

A tab 4441 extends out from a middle of an upper portion of a side of the first guiding bar 444. The tab 4441 is coplanar with a top surface of the first guiding bar 444. The first guiding bar 444 defines a positioning hole 4443 extending through opposite side surfaces of the first guiding bar 444 and below the tab 4441, and defines a plurality of connecting holes 4445 in the top surface. The positioning hole 4443 is tapered toward the side surface below the tab 4441. A diameter of a part of the positioning hole 4443 adjacent to the tab 4441 is less than a diameter of the steel ball 449.

A tab 4452 extends out from an upper portion of a side of the second guiding bar 445, coplanar with a top surface of the second guiding bar 445. The second guiding bar 445 defines a screw hole 4454 extending through opposite side surfaces of the second guiding bar 445 and below the tab 4452, and defines a plurality of connecting holes 4456 in the top surface.

Figure 4:
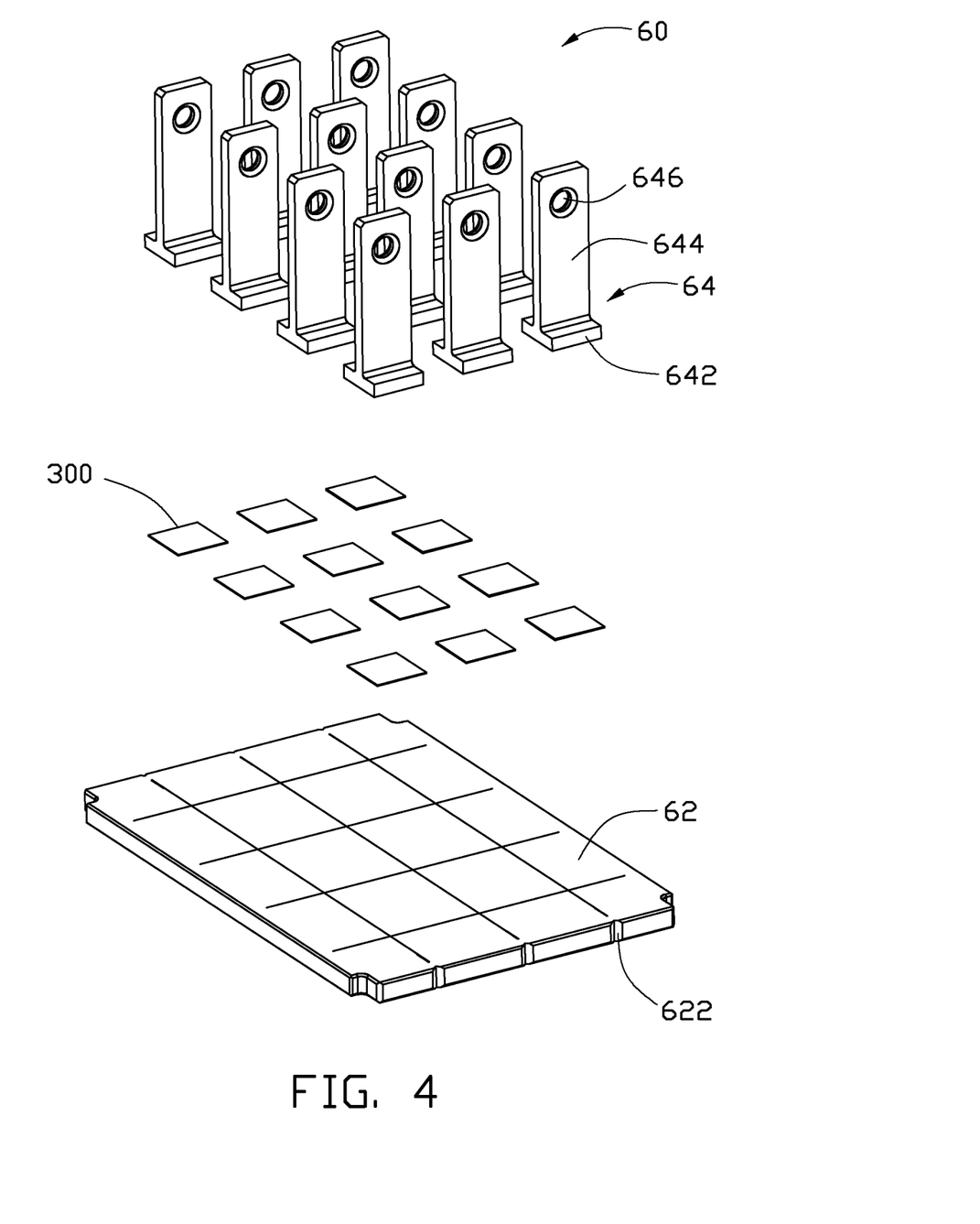
FIG. 4 is an enlarged, isometric view of the positioning apparatus of FIG. 1.

Referring to FIG. 4, the positioning apparatus 60 includes a rectangular supporting plate 62, and a plurality of substantially T-shaped pulling blocks 64. Two opposite end surfaces of the supporting plate 62 each define three positioning slots 622. Each pulling block 64 includes a rectangular pressing portion 642 and a connecting portion 644 substantially perpendicularly extending up from a middle of the pressing portion 642. A distal end of the connecting portion 644 opposite to the pressing portion 642 defines a connecting hole 646.

Figure 5:
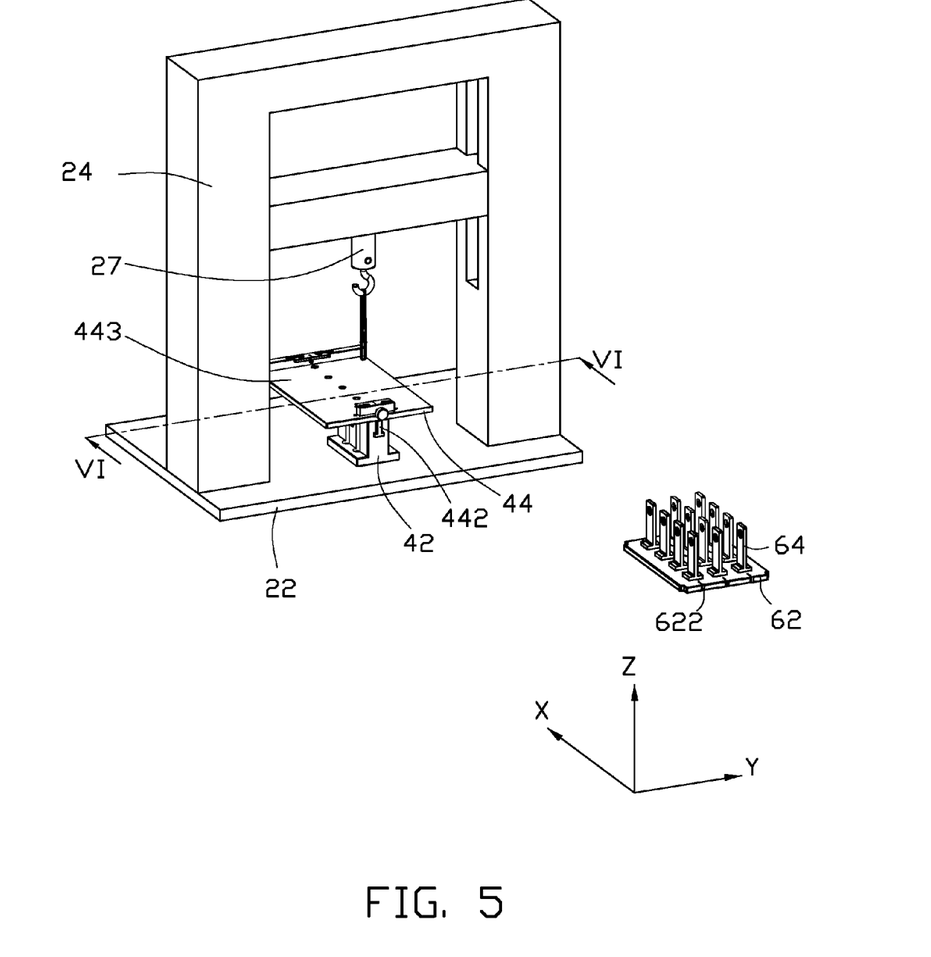
FIG. 5 is a partially assembled, isometric view of FIG. 1.
Figure 6:
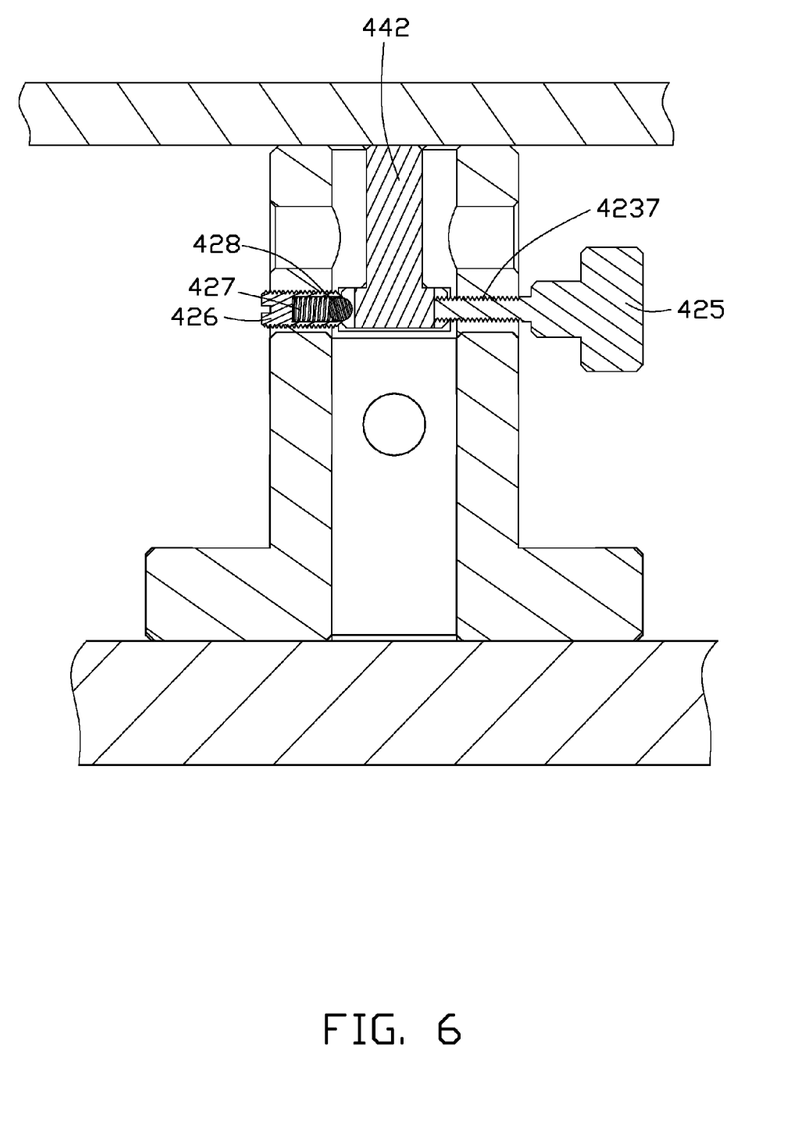
FIG. 6 is a partial, cross-sectional view of FIG. 5, taken along the line of VI-VI.
Figure 7:
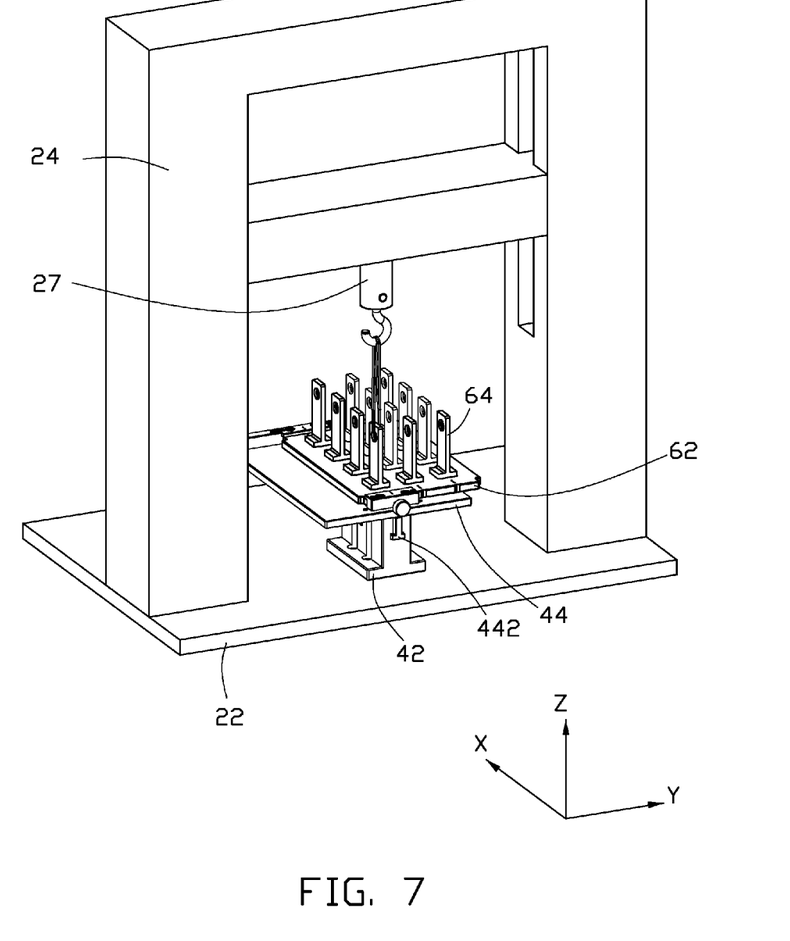
FIGS. 7-9 are assembled, isometric views of the measuring device of FIG. 1, showing different using states.
Figure 8:
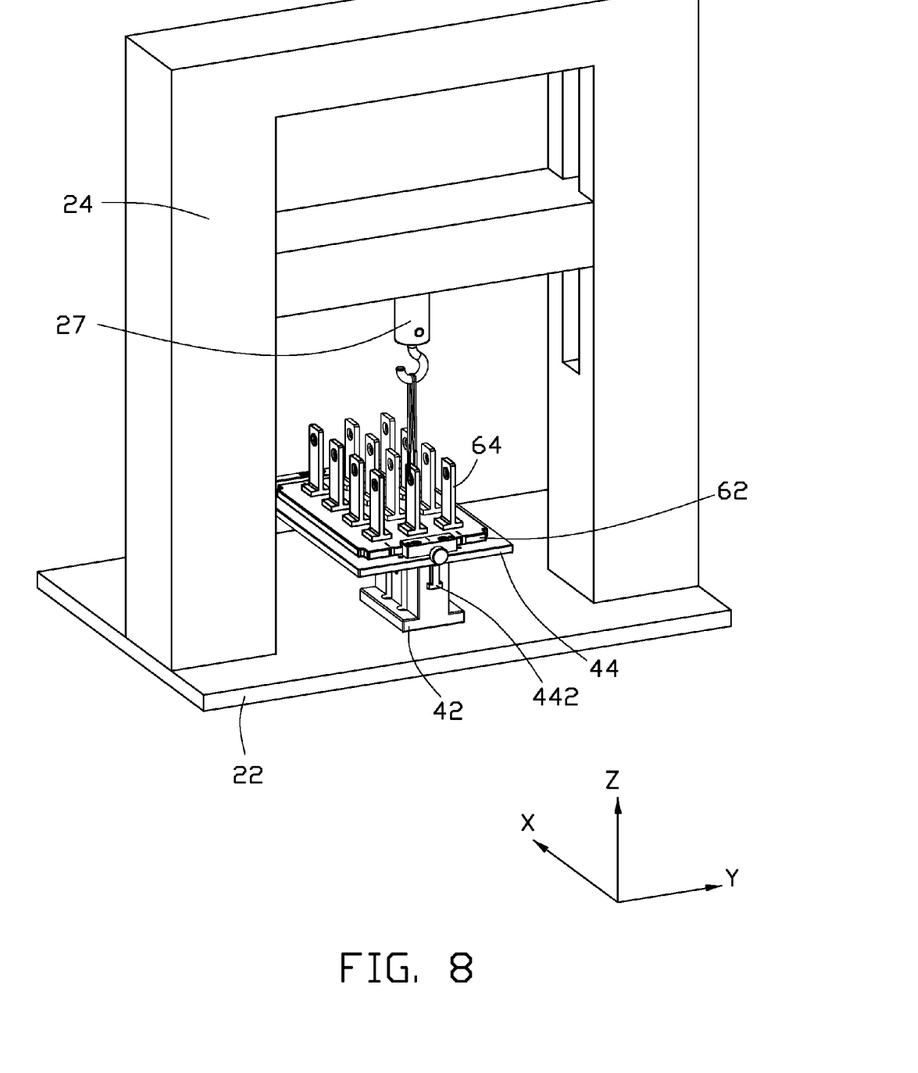
Figure 9:
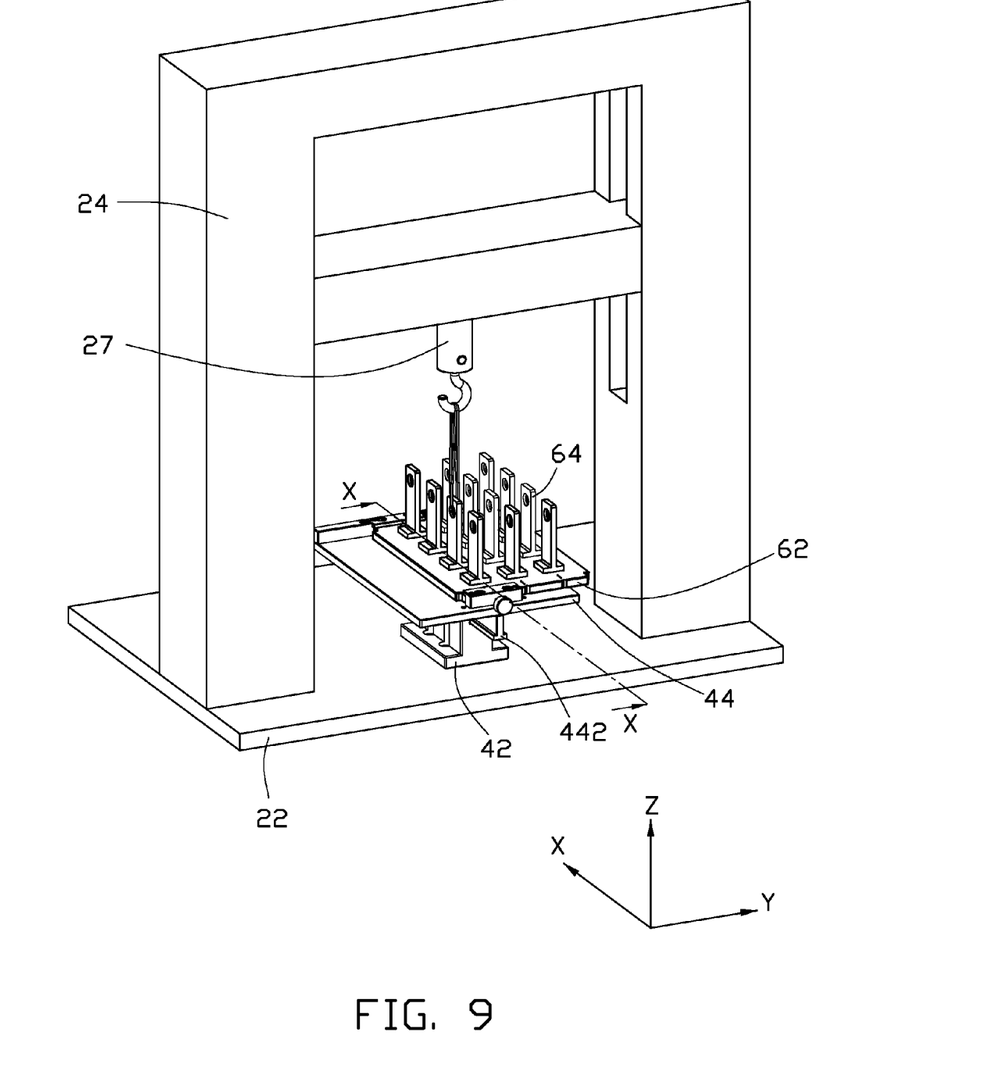
Figure 10:
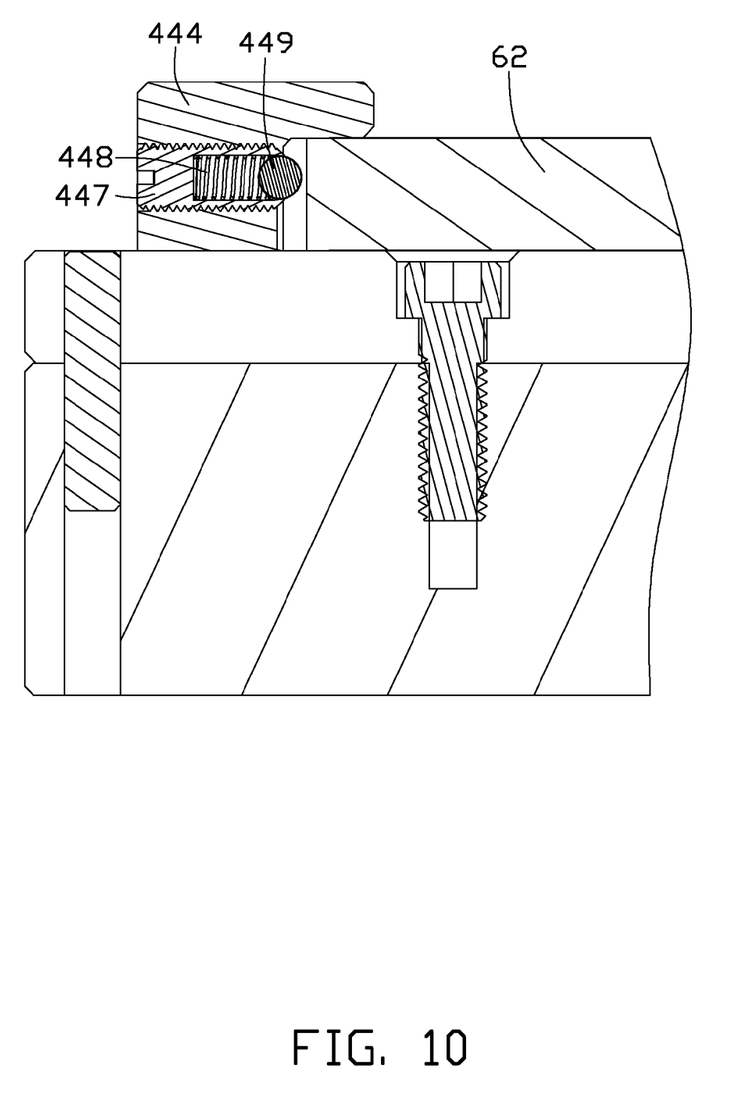
FIG. 10 is a partial, cross-sectional view of FIG. 8, taken along the line of X-X.

Referring to FIGS. 5-6, in assembly, the steel ball 428 and the spring 427 are orderly inserted into the positioning hole 4236 of the base 42 through the corresponding side surface. The positioning screw 426 is screwed into the positioning hole 4236. Opposite ends of the spring 427 respectively abut against the positioning screw 426 and the steel ball 428. A part of the steel ball 428 is exposed out of the positioning hole 4236, and extends into the positioning portion 4233.

The connecting plate 422 of the base 42 is supported on the bottom wall 22 of the frame 20. A plurality of screws extends through the corresponding through holes 4222, to be screwed into the corresponding screw holes 222. The slide slot 4232 is substantially perpendicular to the sliding direction (Z-axis) of the beam 246, and a lengthwise direction of the slide slot 4232 is labeled as X-axis direction shown in FIG. 1.

The steel ball 449 and the spring 448 are orderly inserted into the positioning hole 4443 of the first guiding bar 444 from the side surface opposite to the tab 4441. The positioning screw 447 is screwed into the positioning hole 4443. Opposite ends of the spring 448 respective abut against the positioning screw 447 and the steel ball 449. A part of the steel ball 449 is exposed out of the positioning hole 4443 adjacent to the tab 4441. A plurality of screws extends through the corresponding connecting holes 4445 of the first guiding bar 444, to be screwed into the corresponding screw holes 4412 in a corresponding end of the supporting portion 441, thus fixing the first guiding bar 444 on the supporting portion 441. A plurality of screws extends through the corresponding connecting holes 4456 of the second guiding bar 445, to be screwed into the corresponding screw holes 4412 in the other end of the supporting portion 441, thus fixing the second guiding bar 445 on the supporting portion 441. The tab 4441 faces the tab 4452. The tabs 4441 and 4452, the side surfaces of the first and second guiding bars 444 and 445 below the tabs 4441 and 4452, and the supporting portion 441 cooperatively bound a receiving space 443.

A plurality of screws extends through the stopping holes 4414, to be screwed into the corresponding screw holes 4428, thus fixing the supporting portion 441 on the connecting bar 4424. The rail 442 is inserted into the guiding slot 4232 from one of the end surfaces of the extending portion 423, with the positioning bar 4422 slidably received in the positioning portion 4233, and the connecting bar 4424 slidably received in the guiding portion 4234. The positioning bar 4422 slidably abuts against the steel ball 428 in the positioning portion 4233, and the steel ball 428 withdraws back into the positioning hole 4236 to deform the spring 427. When the steel ball 428 aligns with one of the positioning slots 4426 in one of the side surfaces of the positioning bar 4422, the spring 427 is self-restored to bias the steel ball 428 to latch into the positioning slot 4426. The stopping screw 425 is screwed into the screw hole 4237 of the base 42, with a distal end of the stopping screw 425 passing through the screw hole 4237 to engage in a corresponding positioning slot 4426 in the other side surface of the positioning bar 4422.

Referring to FIGS. 7-10, in use, the adhesive pieces 300 are adhered between the corresponding pressing portions 642 and the supporting plate 62. The pulling blocks 64 are supported on the supporting plate 62, which are arrayed in three lines along the X-axis direction, and are arrayed in four rows along a Y-axis direction perpendicular to the X-axis and Z-axis. A distance of every two adjacent pulling blocks 64 along the X-axis direction is equal to a distance of every two adjacent positioning slots 4426 of the rail 442. Each pulling block 64 is pressed toward the supporting plate 62 with a predetermined pressure for a predetermined time. The supporting plate 62 is slidably inserted into the receiving space 443 along the Y-axis direction. The opposite end surfaces of the supporting plate 62 are slidably engaged with the side surfaces of the first and second guiding bars 444 and 445. The steel ball 449 is abutted against the corresponding end surface of the first guiding bar 444, to withdraw back into the positioning hole 4443. The spring 448 is deformed. When the steel ball 449 aligns with one of the corresponding positioning slots 622 of the supporting plate 62, the spring 448 is self-restored to bias the steel ball 428 to latch into the positioning slot 622. The stopping screw 446 extends through the screw hole 4454 of the second guiding bar 445, to latch into a corresponding positioning slot 622 facing the second guiding bar 445. When the hook 271 is aligned with one of the pulling blocks 64, the rope 272 is extended through the connecting hole 646 of the pulling block 64 and connected to the hook 271. The beam 246 is moved up along the Z-axis direction, the pull member 27 pulls the pulling block 64 up, until the pressing portion 642 of the pulling block 64 is disengaged from the supporting plate 62. Therefore, an adhesive strength of the adhesive piece 300 can be measured, which is equal to a pulling strength of the pull member 27.

When the adhesive strength of another adhesive piece 300 along the X-axis direction needs to be measure, the stopping screw 425 is released from the rail 442. The supporting assembly 44 is moved along the X-axis direction with the rail 442 sliding in the slide slot 4232. The positioning bar 4422 slidably abuts against the steel ball 428, deforming the spring 427, until the steel ball 428 aligns with another positioning slot 4426. The spring 427 is self-restored to bias the steel ball 428 to latch into another positioning slot 4426. The stopping screw 425 screwed again to latch into the corresponding positioning slot 4426. Therefore, the test can be made as described above.

When the adhesive strength of another adhesive piece 300 along the Y-axis direction needs to be measured, the stopping screw 446 is released from the supporting plate 62. The positioning apparatus 60 is moved along the Y-axis direction in the receiving space 443. The supporting plate 62 slidably abuts against the steel ball 449, deforming the spring 448, until the steel ball 449 aligns with another positioning slot 622. The spring 448 is self-restored to bias the steel ball 449 to latch into another positioning slot 622. The stopping screw 446 is screwed again to latch into another positioning slot 622. Therefore, the test can be made as described above.

Even though numerous characteristics and advantages of the embodiments have been set forth in the foregoing description, together with details of the structure and function of the embodiments, the present disclosure is illustrative only, and changes may be made in details, especially in the matters of shape, size, and arrangement of parts within the principles of the embodiments to the full extent indicated by the broad general meaning of the terms in which the appended claims are expressed.

What is claimed is:

1. A measuring device for measuring adhesive strength of two-sided adhesive pieces, the measuring device comprising:
   a frame comprising a rack, and a pull member slidably mounted on the rack along a first direction;
   a supporting apparatus comprising a base fixed to the rack and a supporting assembly slidably installed on the base along a second direction perpendicular to the first direction; and
   a positioning apparatus comprising a supporting plate slidably installed on the supporting assembly along a third direction perpendicular to the first and second directions, and a plurality of pulling blocks, wherein each adhesive piece is adhered between the supporting plate and a corresponding one of the pulling blocks, each pulling block is operable to be connected to the pull member to be pulled along the first direction to disengage from the supporting plate, thus to measure the adhesive strength of the adhesive piece, and
   wherein the frame further comprises a bottom wall, the rack is substantially U-shaped and secured on the bottom wall, a beam being slidably mounted to the rack along the first direction, the pull member is fixed to the beam, wherein the base is fixed on the bottom wall, the base defines a slide slot along the second direction, the supporting assembly comprises a rail slidably received in the slide slot, wherein the supporting assembly comprises a supporting portion, a first guiding bar fixed on a first end of the supporting portion, and a second guiding bar fixed on a second end of the supporting portion opposite to the first guiding bar, the rail is fixed to a bottom of the supporting portion, the supporting portion, the first bar, and the second bar cooperatively bound a receiving space for slidably receiving the supporting plate along the third direction, wherein the first guiding bar defines a positioning hole extending through opposite side surfaces of the first guiding bar and communicating with the receiving space, the supporting assembly further comprises a positioning screw, an elastic member, and a steel ball, a first end of the supporting plate defines a plurality of first positioning slots, the steel ball and the elastic member are orderly inserted into the positioning hole, the positioning screw is screwed into the positioning hole, opposite ends of the elastic member respectively abut against the positioning screw and the steel ball, to bias the steel ball to latch into the corresponding first positioning slot of the supporting plate.

2. The measuring device of claim 1, wherein the base comprises a connecting plate fixed on the bottom wall and an extending portion perpendicularly extending up from a middle of the connecting plate, the slide slot is defined in a center of a top of the extending portion, the slide slot extends through a top and two opposite end surfaces of the extending portion, the rail is slidably inserted into the slide slot from one of the end surface of the extending portion along the second direction.

3. The measuring device of claim 2, wherein the base further comprises a positioning screw, an elastic member, and a steel ball, a first side surface of the extending portion defines a positioning hole communicating with the slide slot, a first side of the rail defines a plurality of first positioning slots, the steel ball and the elastic member are orderly inserted into the positioning hole of the base through the first side surface, the positioning screw is screwed into the positioning hole, opposite ends of the elastic member respectively abut against the positioning screw and the steel ball, to bias the steel ball to latch into the corresponding first positioning slot of the rail.

4. The measuring device of claim 3, wherein the elastic member is a spring.

5. The measuring device of claim 3, wherein a second side surface of the extending portion opposite to the first side surface defines a screw hole communicating with the slide slot, opposite to the positioning hole, a second side of the rail defines a plurality of second positioning slots opposite to the first positioning slots, a stopping screw extends through the screw hole to latch into the corresponding second positioning slot of the rail.

6. The measuring device of claim 1, wherein a tab extends out from a middle of an upper portion of a side of the first guiding bar, for limiting the supporting plate.

7. The measuring device of claim 1, wherein a tab extends out from an upper portion of a side of the second guiding bar for limiting the supporting plate.

8. The measuring device of claim 1, wherein the elastic member is a spring.

9. The measuring device of claim 1, wherein a second end of the supporting plate defines a plurality of second positioning slots opposite to the first positioning slots, the second guiding bar defines a screw hole extending through the side surfaces of the second guiding bar, and communicating with the receiving space, a stopping screw extends through the screw hole to latch into the corresponding second positioning hole of the supporting plate.

* * * * *